(12) United States Patent
Berndl et al.

(10) Patent No.: US 9,149,431 B2
(45) Date of Patent: Oct. 6, 2015

(54) ITRACONAZOLE COMPOSITIONS WITH IMPROVED BIOAVAILABILITY

(71) Applicants: ABBOTT GMBH & CO. KG, Wiesbaden (DE); BARRIER THERAPEUTICS, Princeton, NJ (US)

(72) Inventors: Gunther Berndl, Herxheim am Berg (DE); Matthias Degenhardt, Limburgerhof (DE); Markus Mägerlein, Mannheim (DE); Gerrit Dispersyn, Princeton, NJ (US)

(73) Assignees: Abbvie Deutschland GmbH & Co KG, Wiesbaden (DE); Barrier Therapeutics, Inc., Princeton, NJ (US)

( * ) Notice: Subject to any disclaimer, the term of this patent is extended or adjusted under 35 U.S.C. 154(b) by 0 days.

(21) Appl. No.: 13/923,459

(22) Filed: Jun. 21, 2013

(65) Prior Publication Data

US 2014/0005204 A1    Jan. 2, 2014

Related U.S. Application Data

(62) Division of application No. 11/997,256, filed as application No. PCT/EP2006/007839 on Aug. 8, 2006, now Pat. No. 8,486,456.

(60) Provisional application No. 60/595,816, filed on Aug. 8, 2005.

(51) Int. Cl.
| | |
|---|---|
| *A61K 9/10* | (2006.01) |
| *A61K 31/496* | (2006.01) |
| *A61K 9/14* | (2006.01) |

(52) U.S. Cl.
CPC . *A61K 9/10* (2013.01); *A61K 9/146* (2013.01); *A61K 31/496* (2013.01)

(58) Field of Classification Search
None
See application file for complete search history.

(56) References Cited

U.S. PATENT DOCUMENTS

| | | | |
|---|---|---|---|
| 4,267,179 A | 5/1981 | Heeres et al. | |
| 6,509,038 B2 * | 1/2003 | Baert et al. | 424/480 |
| 2004/0013736 A1 * | 1/2004 | Nakano et al. | 424/489 |
| 2004/0197398 A1 | 10/2004 | Friesen et al. | |
| 2005/0084529 A1 | 4/2005 | Rosenberg et al. | |
| 2009/0028938 A1 | 1/2009 | Berndl et al. | |

FOREIGN PATENT DOCUMENTS

| | | |
|---|---|---|
| EP | 0240904 A2 | 10/1987 |
| EP | 0240906 A2 | 10/1987 |
| EP | 0337256 A2 | 10/1989 |
| EP | 1323416 A1 | 7/2003 |
| WO | 93/19061 | 9/1993 |
| WO | 97/44014 A | 11/1997 |
| WO | 02/24184 A2 | 3/2002 |
| WO | 2004/054568 | 7/2004 |
| WO | 2007017249 | 2/2007 |

OTHER PUBLICATIONS

Verreck et al., "Characterization of solid dispersions of itraconazole and hydroxypropylmethylcellulose prepared by melt extrusion—part I", 2003, International Journal of Pharmaceutics, vol. 251, pp. 165-174.*
Negroni R. et al.: "Itraconazole: Pharmacokinetics and Indications", Archives of Medical Research, Instituto Mexicano Del Seguro Social, Mexico, MX, 1993, pp. 387-393.
Leuner C et al.: "Improving drug solubility for oral delivery using solid dispersions", European Journal of Pharmaceutics and Biopharmaceutics, Elsevier Science Publishers B.V., Amsterdam, NL, 2000, vol. 50, No. 1, pp. 47-60, XP00425779, ISSN: 0939-6411.
Verreck G. et al.: "Characterization of solid dispersions of itraconazole and hydroxypropylmethylcellulose prepared by melt extrusion: Part I", International Journal of Pharmaceutics, Amsterdam, NL. vol. 251, No. 1-2, pp. 165-174, XP002406057, ISSN: 0378-5173, the whole document.
International Search Report issued on Feb. 12, 2008 for International Patent Application No. PCT/EP2006/007840.
International Preliminary Report on Patentability issued on Feb. 12, 2008 for International Patent Application No. PCT/EP2006/007840.
Written Opinion issued on Feb. 12, 2008 for International Patent Application No. PCT/EP2006/007840.
International Preliminary Report on Patentability (Form PCT/IB/373) issued on Feb. 21, 2008 in International Patent Application No. PCT/EP2006/007839.

* cited by examiner

*Primary Examiner* — Michael B Pallay
(74) *Attorney, Agent, or Firm* — Saul Ewing LLP; Peter C. Lauro, Esq.

(57) ABSTRACT

A solid dispersion product comprising itraconazole and hydroxypropyl methylcellulose, which satisfies the Formula $0.35 > \Delta H_{tr}$ (1) (wherein $\Delta H_{tr}$ represents the endotherm (J/g) accompanying a transition at about 240° C.). The solid dispersion product shows an improved bioavailability.

11 Claims, 1 Drawing Sheet

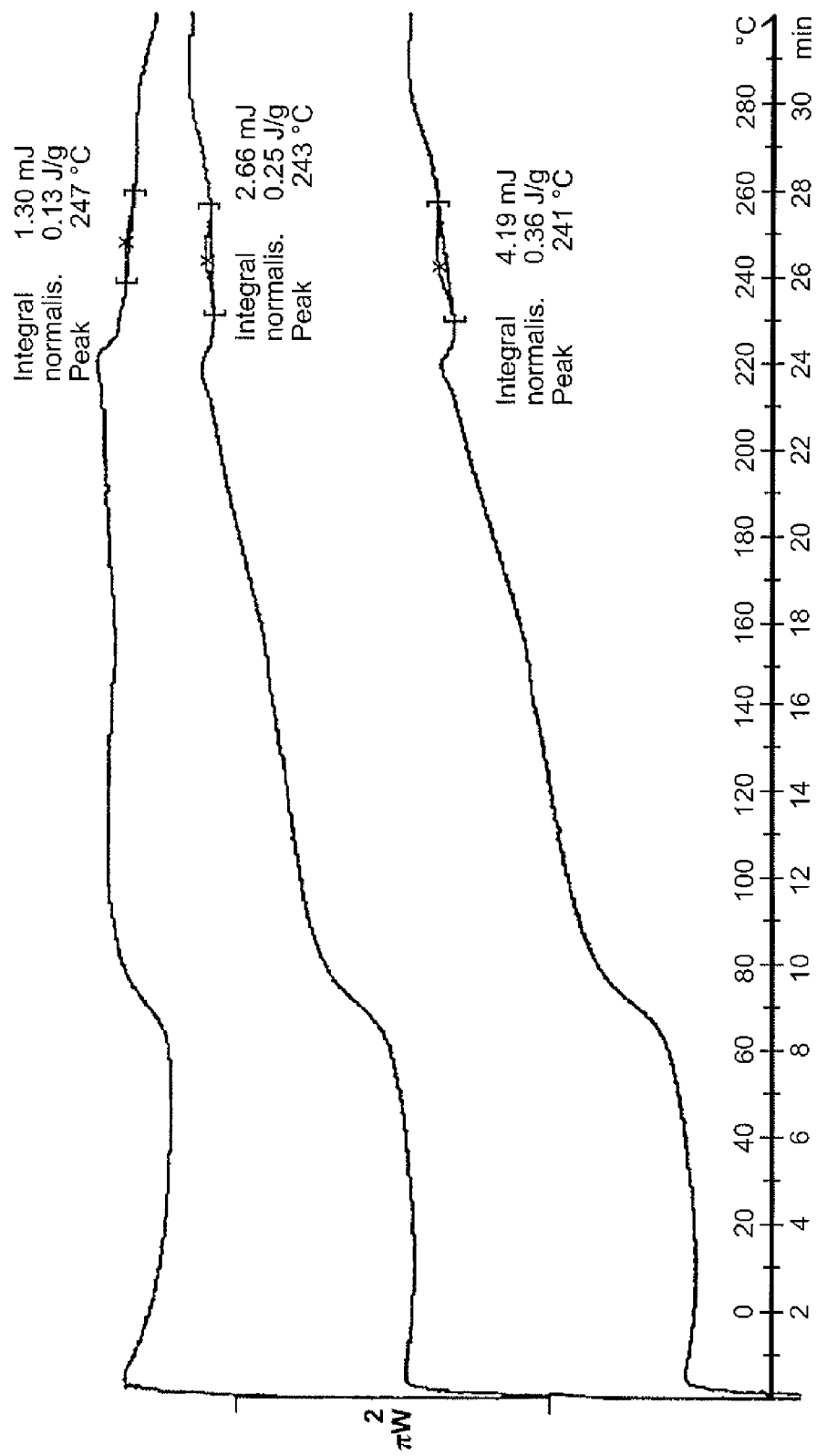

ITRACONAZOLE COMPOSITIONS WITH IMPROVED BIOAVAILABILITY

This application is a divisional application of U.S. application Ser. No. 11/997,256, now U.S. Pat. No. 8,486,456, which is the U.S. national phase, pursuant to 35 U.S.C. §371, of PCT international application Ser. No. PCT/EP2006/007839, filed Aug. 8, 2006, designating the United States and published in English on Feb. 15, 2007 as publication WO 2007/017248 A2, which claims priority to U.S. provisional patent application Ser. No. 60/595,816, filed Aug. 8, 2005. The entire contents of the aforementioned patent applications are incorporated herein by this reference.

The present invention relates to novel pharmaceutical compositions of itraconazole as well as to a process for their preparation. The development of pharmaceutical compositions having good bioavailability of itraconazole, a compound that is practically insoluble in aqueous media, remains one of the main challenges of pharmaceutical development of this compound. Itraconazole or (+)-cis-4-[4-[4-[4-[[2-(2,4-dichlorophenyl)-2-{1H-1,2,4-triazol-1-yl-methyl)-1,3-dioxoian-4-yl]methoxy]phenyl]-1-piperazinyl]phenyl]-2,4-dihydro-2-(1-methylpropyl)-3H-1,2,4-triazol-3-one, is a broadspectrum antifungal compound developed for oral, parenteral and topical use and is disclosed in U.S. Pat. No. 4,267,179.

WO 97/44014 discloses an itraconazole composition that comprises particles which are obtainable by melt-extruding a mixture comprising itraconazole and an appropriate water-soluble polymer, such as hydroxypropyl methylcellulose, and subsequently milling the melt-extruded mixture. These compositions exhibited an improved bioavailability of itraconazole over the oral dosage forms of itraconazole known at the time.

Nevertheless, it is desirable to provide dosage forms of itraconazole with still greater bioavailability. This objective is met by a solid dispersion product comprising itraconazole and hydroxypropyl methylcellulose, which satisfies the formula $$0.35 > \Delta H_{tr}$$

(wherein $\Delta H_{tr}$ represents the endotherm (J/g) accompanying a transition at an endothermic peak temperature in the range of from about 240° C. to about 250° C.).

Preferably, the solid dispersion product satisfies the formula $$0.20 > \Delta H_{tr}$$

More preferably, the solid dispersion product satisfies the formula $$0.15 > \Delta H_{tr}$$

The $\Delta H_{tr}$ is determined by differential scanning calorimetry (DSC) measurement. More specifically, a melting endotherm curve is first prepared by the following method using a differential scanning calorimeter. A finely ground sample of the dispersion product is placed in an open aluminium pan of a differential scanning calorimeter. The endotherm between −20° C. and 300° C. is obtained by heating the sample at a temperature rise rate of 10° C./minute. A maximum peak is observed in the thus prepared melting endotherm curve in the range of from about 240° C. to about 250° C. (in the following also referred to as "endotherm at about 240° C."), and the change rate of enthalpy observed thereupon, in terms of Joules per one gram of solid dispersion product, is determined to be the endotherm $\Delta H_{tr}$. The change rate of enthalpy corresponds to the area enclosed between the peak and the interpolated base line.

The invention further relates to a pharmaceutical dosage form comprising a solid dispersion product of itraconazole and hydroxypropyl methylcellulose, the dosage form providing in vivo plasma levels of itraconazole and hydroxy itraconazole (combined) characterized by $C_{max}$ of 400 ng/mL or higher, preferably 450 ng/mL or higher, after oral administration of a single dose of 200 mg itraconazole. "$C_{max}$" designates the peak plasma concentration observed after oral administration to a human. Itraconazole and hydroxy itraconazole levels in the plasma may be assessed by any art-accepted method.

The term "solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase (as defined in thermodynamics), such a dispersion is called a "solid solution". Solid solutions are preferred physical systems because the components therein readily form liquid solutions when brought into contact with a liquid medium such as gastric juice. This increased propensity for dissolution may be attributed at least in part to the fact that the energy required for dissolving the components from a solid solution is less than that required for dissolving the components from a crystalline or microcrystalline solid phase.

The term "solid dispersion product" also comprises dispersions which are less homogeneous throughout than solid solutions. Such dispersions are not chemically and physically uniform throughout or comprise more than one phase. These encompass systems having small particles, typically of less than 1 ^m in diameter, of itraconazole dispersed in a matrix of hydroxypropyl methylcellulose, as well as systems having small particles of itraconazole dispersed in a matrix of a solid solution of itraconazole in hydroxypropyl methylcellulose. Preferred systems are those wherein the itraconazole is in an essentially non-crystalline phase as these have an intrinsically faster dissolution rate than those wherein part or all of the itraconazole is in a microcrystalline or crystalline form. The absence of microcrystalline or crystalline itraconazole forms may be ascertained by thermal analysis (DSC) or X-ray diffraction analysis (WAXS).

Without wishing to be bound to theory, we believe that polymer "melting" from a crystalline state to nematic "liquid" state generally uses a route which includes a passage via a mesomorphic (liquid crystalline) phase. If the starting hydroxypropyl methylcellulose is incompletely "molten" some mesomorphic domains remain in the polymeric matrix.

We believe that the mesomorphic domains have thermodynamic properties which place them intermediate between melt and crystals and, hence, the endotherm observed at about 240° C. is attributable to the latent heat of transition, i.e., the melting of the mesomorphic domains. The lower the change rate of enthalpy, the lower the proportion of mesomorphic domains in the formulation and the more homogeneous the polymeric matrix. High bioavailability appears to be linked to a highly homogeneous matrix.

Four diastereoisomers of itraconazole exist, the preparation and utility of which are disclosed in WO 93/19061. The preferred itraconazole compound is the (±)-(2R*,4S*) or cis forms of the free base, having the Chemical Abstracts Registry Number [8462561-6], The term "itraconazole" as used herein shall include any of its stereoisomers or a mixture of two or three or four of its stereoisomers.

Instead of the itraconazole free base, acid addition salts thereof may be used. The acid addition salts may be obtained by reacting the free base with an appropiate acid. Appropiate acids may include, for example, inorganic acids such as hydrohalic acids, e.g. hydrochloric or hydrobromic acid, sulfuric acid; nitric acid; phosphoric acid and the like; or organic acids such as, for example, formic, acetic, propanoic, hydroxyacetic, 2-hydroxypropanoic, 2-oxopropanoic, ethanedioic, propanediol, butanedioic, (Z)-butanedioic, (E)-butanedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and like acids.

The hydroxpropyl methylcellulose (HPMC) used in carrying out the invention contains a sufficient number of hydroxypropyl and methoxy groups to render it water-soluble.

The total content of methoxy and hydroxypropyl groups is preferably in the range of 23 to 42% by weight. More preferably, the total content of methoxy and hydroxypropyl groups is in the range of 30 to 42% by weight. Preferably, the methoxy group content is in the range of 19 to 30 wt % (in particular 28 to 30 wt %) and the hydroxypropyl group content is in the range of 4 to 12 wt % (in particular 7 to 12 wt %).

Hydroxypropyl methylcellulose is also known as hypromellose (see Martindaie, The Extra Pharmacopoeia, 29$^{th}$ edition (Pharmaceutical Press, 1989) page 1435). For HPMC, three types are commercially available: HPMC 2208, HPMC 2906, and HPMC 2910, depending on the contents of methoxy and hydroxypropyl groups. In the four digit number associated with HPMC as described by Martindale, the first two digits represent the approximate percentage of methoxy groups and the third and fourth digits the approximate percentage composition of hydroxypropyl groups, it is specified that hydroxypropyl methyl cellulose 2208 contains 19 to 24 wt % of methoxy groups and 4 to 12 wt % of hydroxypropyl groups in a total of 23 to 36 wt %; hydroxypropyl methyl cellulose 2906 contains 27 to 30 wt % of methoxy groups and 4 to 7.5 wt % of hydroxypropyl groups in a total of 31 to 37.5 wt %, and hydroxypropyl methyl cellulose 2910 contains 28 to 30 wt % of methoxy groups and 7 to 12 wt % of hydroxypropyl groups in a total of 35 to 42 wt %. Any of these celluloses may be used in the practice of the invention, with HPMC 2910 being especially preferred.

The molecular weight of the HPMC normally affects both the release profile of the milled extrudate as well as its physical properties. A desired release profile can thus be designed by choosing an HPMC of an appropriate molecular weight. For immediate release of the active ingredient from the particles, a low molecular weight polymer is preferred. A high molecular weight HPMC is more likely to yield a sustained release pharmaceutical dosage form. The molecular weight of a water-soluble cellulose ether, such as HPMC, is generally expressed in terms of the apparent viscosity of an aqueous solution containing two percent by weight of said cellulose ether at 20° C. Suitable HPMCs include those having a viscosity from about 1 to about 100 mPa·s, more preferably from about 3 to about 15 mPa·s, and most preferably at about 5 mPa·s. The most preferred type of HPMC having a viscosity of 5 mPa·s is the commercially available HPMC 2910 5 mPa·s.

Although it is believed that the particle size distribution of the HPMC starting material is of secondary influence to the properties of solid dispersion product, the HPMC starting material preferably has a size distribution (as determined using laser light diffraction; Malvern Mastersizer) with $d_0.5$ of not more than 125 (and, more preferably of not more than 100. Preferably, $d_0.g$ is not more than 300^m, more preferably not more than 245 (jm.

Preferably, the weight ratio of itraconazole:hydroxypropyl methylcellulose is in the range of 1:1 to 1:17, more preferably 1:1 to 1:5, In the case of (itraconazole):(HPMC 2910 5 mPa·s), this ratio may range from about 1:1 to about 1:2 and is optimally about 1:1.5 (or 2:3). The lower limit is determined by practical considerations, indeed, given that the therapeutically effective amount of itraconazole is from about 50 mg to about 400 mg per day, preferably 200 mg per day, the lower limit ratio is determined by the maximum amount of mixture that can be processed into one dosage form of a practical size. When the relative amount of water-soluble polymer exceeds the upper acceptable range, the absolute amount of mixture needed to achieve a therapeutic level will be too great to be processed into one capsule or tablet. Tablets, for example, can have a maximum weight of about 1 gram, of which a maximum of 90% (w/w) can be the extrudate. In this case, the lower limit of the amount of itraconazole compared to hydroxypropyl methylcellulose will be about 1:17 (i.e., 50 mg itraconazole and 50 mg polymer).

As the ratio of itraconazole:hydroxypropyl methylcellulose increases (i.e. the amount of itraconazole increases relative to the amount of polymer), then there is the risk that the itraconazole will not dissolve sufficiently in the polymer and thus that the required bioavailability will not be obtained. The degree to which a compound has dissolved in a water-soluble polymer can often be checked visually. If the extrudate is clear, then it is likely that the compound has dissolved completely in the water-soluble polymer. The 1:1 itraconazole:hydroxypropyl methylcellulose upper limit is determined by the fact that it has been observed that, at this ratio, the extrudate resulting from extruding itraconazole with HPMC 2910 5 mPa·s was not "clear", presumably due to the fact that not all of the itraconazole had dissolved in the HPMC. It will be appreciated that the upper limit of 1:1 may be an underestimate for other types of HPMC.

The solid dispersion product of the invention is prepared by a melt-extrusion process.

The melt-extrusion process typically comprises the following steps:
a) blending itraconazole and hydroxypropyl methylcellulose;
b) heating the blend to obtain a homogenous melt,
c) forcing the thus obtained melt through one or more nozzles; and
d) allowing the melt to solidify to obtain a solid dispersion product.

Specifically, the method comprises the following steps:
a) blending itraconazole and a hydroxypropyl methylcellulose or a mixture of two or more hydroxypropyl methylcelluloses;
b) heating the blend, under preset conditions of temperature, shear and throughput rate, to obtain a homogeneous melt;
c) forcing the thus obtained melt through one or more nozzles;
d) allowing the melt to solidify to obtain a solid dispersion product;
e) subjecting a representative sample of the obtained solid dispersion product to differential scanning calorimetry measurement; and, if necessary,
f) adjusting the conditions of temperature, shear and throughput rate used in step b) such that the solid dispersion product satisfies the formula $$0.35 > \Delta H_{tr},$$

preferably $0.20 > \Delta H_{tr}$,
more preferably $0.15 > \Delta H_t$, (wherein $\Delta H_{tr}$ represents the endotherm (J/g) accompanying a transition at an endothermic peak temperature in the range of from about 240° C. to about 250° C.

The terms "melt" and "melting" should be interpreted broadly. For our purposes, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which, upon cooling, may form a solid solution having advantageous dissolution properties.

The melting and/or mixing takes place in an apparatus customarily used for this purpose. Particularly suitable are extruders or kneaders. Suitable extruders include single screw extruders, intermeshing screw extruders or else multi-screw extruders, preferably twin screw extruders, which can be corotating or counterrotating and are optionally equipped with kneading disks. The heart of any twin-screw compounding extruder is its screws. Typically, the screws comprise forward-flighted elements to convey the materials; further, they may comprise reverse-flighted elements to create pressure fields, and kneaders and shear elements to exert a kneading action to the melt. Screws can be made shear intensive or less aggressive based on the number and type of shearing elements integrated into the screw program.

The melt ranges from pasty to viscous. Before allowing the melt to solidify, the melt may be moulded into virtually any desired shape. The shaping of the extrudate is conveniently carried out by a calender with two counter-rotating rollers with mutually matching depressions on their surface. A broad range of tablet forms can be attained by using rollers with different forms of depressions. Alternatively, the extrudate is cut into pieces, either before (hot-cut) or after solidification (cold-cut).

In one embodiment the melt is extruded through a slot die to obtain a film. The film thus obtained is optionally stretched, axially or biaxially. The film can be cut into the desired size.

It has been found that the energy input during melt-extrusion production is important for good bioavailability. Based upon the results of the examples that follow, it is postulated that the higher the energy input in the extrusion process, the better the dispersion of itraconazole in the matrix. A lower endotherm at 240° C. is indicative of better dispersion.

One of the most important parameters governing energy input during the melt-extrusion process is the temperature at which the melt-extruder is operating and the temperature at which the nozzle, through which the melt is forced, is kept. The temperature may vary along the length of the extruder barrel. For the purposes herein, the "operating temperature" is the highest temperature the mixture encounters during its passage through the extruder. It was found that the operating temperature should range between about 195° C. and about 300° C. At temperatures lower than 195° C., the extrudate will not have the required bioavailability. In addition, the process is difficult because of the high viscosity of the mixture. At temperatures of more than 300° C. the hydroxypropyl methylcellulose may decompose to an unacceptable level. It should be noted that there is no need to fear decomposition of itraconazole at temperatures up to 300° C., since this active ingredient is thermally very stable. The working temperatures will also be determined by the kind of extruder or the kind of configuration within the extruder that is used.

The throughput rate is also of importance. The longer the mixture remains in contact with the heating element, the higher the energy input. Although most of the energy needed to melt, mix and dissolve the components in the extruder is usually provided by the heating elements, the friction of the material within the extruder may also provide a substantial amount of energy to the mixture and aid in the formation of a homogenous melt of the components. Thus, variation of the screw speed of the extruder has an impact on the energy input. We have found that typically a screw speed of more than 80 revolutions per minute, preferably of more than 100 revolutions per minute up to 350 revolutions per minute, is required to bring about sufficient mixing and shearing.

In the method of the invention it is preferred that the melt is subjected to a kneading action in a kneading section of the extruder. The kneading section may be equipped with kneading disks or rotor blades.

It will be appreciated that, based on the explanation above and the examples that follow, the person skilled in the art will be able to select appropriate parameters for the melt extrusion process to produce extrudates that satisfy the above formula pertaining to $\Delta H_{tr}$.

The solid dispersion product may further comprise one or more pharmaceutically acceptable excipients such as, for example, plasticizers, surfactants, flavors, colorants, preservatives and the like. Said excipients should not be heat-sensitive, in other words, they should not show any appreciable degradation or decomposition at the working temperature of the melt-extruder.

The amount of plasticizer is preferably small, in the order of 0% to 15% (w/w), preferably less than 5% (w/w). In particular, no plasticizer is present in the solid dispersion product. Plasticizers as mentioned hereinbelow lower the temperature at which a melt of itraconazole, hydroxypropyl methylcellulose and plasticizer is formed; this lowering of the melting point is sometimes advantageous. Suitable plasticizers are pharmaceutically acceptable and include low molecular weight polyalcohols such as ethylene glycol, propylene glycol, 1,2-butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as sorbitol lactate, ethyl lactate, butyl lactate, ethyl glycolate, allyl glycollate; and amines such as monoethanolamine, diethanolamine, triethanolamine, monoisopropanolamide; triethylenetetramine, 2-amino-2-methyl-1,3-propanediol and the like. Among these, the low molecular weight polyethylene glycols, ethylene glycol, low molecular weight polypropylene glycols and especially propylene glycol are preferred.

The term "pharmaceutically acceptable surfactant" refers to a pharmaceutically acceptable non-ionic surfactant. The surfactant may effect an instantaneous emulsification of the active ingredient released from the dosage form and prevent precipitation of the active ingredient in the aqueous fluids of the gastrointestinal tract. Preferred surfactants are selected from: polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether or polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate or PEG-300 dioleate; alkylene glycol fatty acid mono esters, e.g. propylene glycol monolaurate (Lauroglycol®); sucrose fatty acid esters, e.g. sucrose monostearate, sucrose distearate, sucrose monolaurate or sucrose dilaurate; sorbitan fatty acid mono esters such as sorbitan mono laurate (Span® 20), sorbitan monooleate, sorbitan monopalmitate (Span® 40), or sorbitan stearate, polyoxyethylene castor 35 oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40) or polyethylenglycol 60 hydrogenated castor oil (Cremophor® RH 60); or block copolymers of ethylene oxide and propylene oxide, also known as polyoxyethylene polyoxypropylene block copolymers or polyoxyethylene polypropyleneglycol such as Poloxamer® 124, Poloxamer® 188, Poloxamer® 237, Poloxamer® 388, or Poloxamer® 407 (BASF Wyandotte Corp.); or mono fatty acid esters of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20), or mixtures of one or more thereof.

The solid dispersion product is preferably milled or ground to particles having a particle size of less than 600 jam, preferably less than 400 p.m and most preferably less than 125 jam. The particle size proves to be an important factor in determining the speed at which tablets having sufficient hardness can be manufactured on a large scale; the smaller the particles, the higher the tabletting speed can be without detrimental effects on their quality. The particle size distribution is such that more than 70% of the particles (measured by weight) have a diameter ranging from about 50 |j.m to about 500 jj.m, in particular from about 50 nm to about 200 nm and especially from about 50 nm to about 125 nm. Particles with the dimensions mentioned herein can be obtained by sieving them through nominal standard test sieves as described in the CRC Handbook, 64$^{th}$ ed., page F-114. Nominal standard sieves are characterized by the mesh/hole width (jim), DIN 4188 (mm), ASTM E 11-70 (No), Tyier(R) (mesh) or BS 410 (mesh) values. Throughout this description, particle sizes are designated by reference to the mesh/hole width in ^m and to the corresponding Sieve No. in the ASTM E11-70 standard.

Once the extrudate is obtained, it is milled and sieved and used as a "normal" ingredient to make pharmaceutical dosage forms.

The particles of the solid dispersion product can be formulated into pharmaceutical dosage forms comprising a therapeutically effective amount of particles. Although mainly pharmaceutical dosage forms for oral administration such as tablets and capsules are envisaged, the particles of the present invention can also be used to prepare pharmaceutical dosage forms e.g. for rectal administration. Preferred dosage forms are those adapted for oral administration shaped as a tablet. They can be produced by conventional tabletting techniques with conventional ingredients or excipients and with conventional tabletting machines, in addition, they can be produced at substantially lower cost than the coated cores. An effective antifungal daily dose of itraconazole ranges from about 50 mg to about 300 mg o.d., and is preferably about 200 mg o.d. Preferably, the (milled) solid dispersion product accounts for not less than 40 wt. % of the weight of the final dosage form, in particular from 45 to 90 wt. %.

In order to facilitate the swallowing of such a dosage form by a mammal, it is advantageous to give the dosage form, in particular tablets, an appropriate shape. Tablets that can be swallowed comfortably are therefore preferably elongated rather than round in shape. Especially preferred are biconvex oblate tablets. As discussed below in more detail, a film coat on the tablet further contributes to the ease with which it can be swallowed.

Tablets that give an immediate release of itraconazole upon oral ingestion and that have good bioavailability are designed in such a manner that the tablets disintegrate rapidly in the stomach (immediate release) while keeping the particles liberated in the process away from one another so that they do not coalesce, create local high concentrations of itraconazole and increase the chances that the drug precipitates (bioavailability). The desired effect can be obtained by distributing said particles homogeneously throughout a mixture of a disintegrant and diluent.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose (crosslinked sodium carboxymethylcellulose). The amount of disintegrant in immediate release tablets according to the present invention may conveniently range from about 3 to about 15% (w/w) and is preferably about 7 to 9%, in particular about 8.5% (w/w). This amount tends to be greater in tablets in order to ensure that the particles are spread throughout a large volume of the stomach contents upon ingestion. Because disintegrants by nature yield sustained release formulations when employed in bulk, it is advantageous to dilute them with an inert substance called a diluent or fitter.

A variety of materials may be used as diluents or fillers. Examples are spray-dried or anhydrous lactose, sucrose, dextrose, mannitol, sorbitol, starch, cellulose (e.g. microcrystalline cellulose Avicel®), dihydrated or anhydrous dibasic calcium phosphate, and others known in the art, and mixtures thereof. A commercial spray-dried mixture of lactose monohydrate (75%) with microcrystalline cellulose (25%), which is commercially availble as Microcelac®, is preferred. The amount of diluent or filler in the tablets may conveniently range from about 20% to about 40% (w/w) and preferably ranges from about 25% to about 32% (w/w).

The tablet may include a variety of one or more other conventional excipients such as binders, buffering agents, lubricants, glidants, thickening agents, sweetening agents, flavors, and colors. Some excipients can serve multiple purposes.

Lubricants and glidants can be employed in the manufacture of certain dosage forms, and will usually be employed when producing tablets. Examples of lubricants and glidants are hydrogenated vegetable oils, e.g. hydrogenated Cottonseed oil, magnesium stearate, stearic acid, sodium lauryl sulfate, magnesium lauryl sulfate, colloidal silica, talc, mixtures thereof, and others known in the art. Interesting lubricants and glidants are magnesium stearate, and mixtures of magnesium stearate with colloidal silica. A preferred lubricant is hydrogenated vegetable oil type I, most preferably hydrogenated, deodorized Cottonseed oil (commercially available from Karlshamns as Akofine NF® (formerly called Sterotex®). Lubricants and glidants generally comprise 0.2 to 7.0% of the total tablet weight.

Other excipients such as coloring agents and pigments may also be added to the tablets of the present invention. Coloring agents and pigments include titanium dioxide and dyes suitable for food. A coloring agent is an optional ingredient in the tablet of the present invention, but, when used, the coloring agent can be present in an amount of up to 3.5% based on the total tablet weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oils, including lemon, orange, grape, lime and grapefruit, and fruit essences, including apple, banana, pear, peach, strawberry, raspberry, cherry, plum, pineapple, apricot and so forth. The amount of flavor may depend on a number of factors including the organoleptic effect desired. Generally the flavor will be present in an amount of from about 0% to about 3% (w/w).

As known in the art, tablet blends may be dry-granulated or wet-granulated before tabletting. The tabletting process itself is otherwise standard and readily practised by moulding a tablet from a desired blend or mixture of ingredients into the appropriate shape using a conventional tablet press.

Tablets of the present invention may further be film-coated to improve taste or provide ease of swallowing and an elegant appearance. Many suitable polymeric film-coating materials are known in the art. A preferred film-coating material is hydroxypropyl methylcellulose HPMC, especially HPMC 2910 5 mPa·s. Other suitable film-forming polymers also may be used herein, including hydroxypropylcellulose and acrylate-methacrylate copolymers. Besides a film-forming polymer, the film coat may further comprise a plasticizer (e.g. propylene glycol) and, optionally, a pigment (e.g. titanium dioxide). The film-coating suspension also may contain talc as an anti-adhesive. In immediate release tablets according to the invention, the film coat is small and in terms of weight accounts for less than about 3% (w/w) of the total tablet weight.

Preferred dosage forms are those wherein the weight of the particles is at least 40% of the total weight of the total dosage form, the weight of the diluent ranges from 20 to 40%, and the weight of the disintegrant ranges from 3 to 10%, the remainder being accounted for by one or more of the excipients described above.

Preferred dosage forms according to the present invention are those from which at least 85% of the available itraconazole dissolves within 60 minutes when a dosage form equivalent to 200 mg itraconazole is tested as set forth in USP test <711> in a USP-2 dissolution apparatus under conditions at least as stringent as the following: 900 ml phosphate buffer, pH 6.0, 37° C. with paddles turning at 100 rpm. Tablets complying with the preceding definition can be said to have Q>85% (60 minutes). Preferably, tablets according to the present invention will dissolve faster and have Q>85% (15 minutes), more preferably Q>85% (5 minutes).

Further, this invention concerns a solid dispersion product as described above for use in preparing a pharmaceutical dosage form for oral administration to a mammal suffering from a fungal infection. Preferably, a single such dosage form can be administered once daily to said mammal. Preferably, said dosage form can be administered at any time of the day regardless of the food taken in by said mammal.

The present invention also concerns the use of a solid dispersion product as described above for the preparation of a pharmaceutical dosage form for oral administration to a mammal suffering from a fungal infection, wherein a single such dosage form can be administered once daily to said mammal.

Subjects afflicted with a fungal infection that may be treated with the dosage forms described herein include both human subjects and animal subjects (particularly mammalian subjects such as dogs, cats and rabbits). Disorders with which such subjects may be afflicted include blastomycosis (pulmonary and extrapulmonary), histoplasmosis (including chronic cavitary pulmonary disease and disseminated, non-meningeal histoplasmosis), aspergillosis (pulmonary and extrapulmonary), onychomycosis (of the toe-nail and/or fingernail), tinea pedis, dermatophytosis (Ringworm), malessezia/yeast dermatitis, cryptococcosis ("window washers disease), candidiasis, coccidiodomycosis ("valley fever"), chromoblastomycosis, fungal menigitis, and oral mucositis. The dosage of itraconazole will vary depending upon factors such as the disease and severity thereof, the age, weight and condition of the subject, etc., but in general is between 50 or 100 milligrams per day up to 800 or 1000 milligrams per day.

It has been observed that the tablets of the present invention exhibited a remarkably lower food-effect than the prior art Sporanox® capsules. This means that the difference between taking the medication after a meal and taking the medication on an empty stomach is significantly less when the tablet of the present invention is administered than when Sporanox® capsules are administered. This is, of course, a huge advantage because the medication can be taken at any time during the day and is no longer dependent upon the intake of a meal.

Moreover, patients who are feeling nauseous or who are not able to eat can still take the tablets of the present invention.

The accompanying FIGURE and the following examples will serve to further illustrate the invention without limiting it.

FIG. 1 shows the DSC thermograms of three different solid dispersion products manufactured at different energy input. The top graph relates to the sample prepared at the highest energy input, the bottom graph relates to the sample prepared at the lowest energy input. The higher the energy input during manufacture, the lower the endotherm (J/g) accompanying the endothermic peak in the range of from 240° C. to 250° C.

EXAMPLE 1

A 40/60 (w/w) mixture of itraconazole (21.74 kg) and hydroxypropyl methylcellulose 2910 5 mPa·s (supplied by Janssen and produced by Dow Chemical in their Midland plant; size distribution as determined using laser light diffraction (Malvern Mastersizer) with $d_{0.1}$=38 μm, $d_{0.5}$=119 μm, $d_{0.5}$=256 μm) was sieved and mixed in a planetary mixer until the mixture was homogenous.

This physical mixture of itraconazole and HPMC was fed into a twin screw melt extruder of the type ZSK 40 (Werner & Pfleiderer) having the following operating parameters: the temperature of the first, second and third compartment was 20° C., 190° C., and 190° C., respectively, the temperature of the transitional section was 190° C., the temperature at the die was 197° C.; the twin screw had a rate of 200 or 250 revolutions/min, respectively. The throughput was 22 kg/h.

The extrudate was placed in a hammer mill of type Fitzmill, at 4736 rpm with a sieve mesh of 0.51 mm. The fraction of particles with a size<125 μm was isolated by further sieving through a No. 120 sieve (ASTM E 11-70); yield<10%.

A spray-dried mixture of lactose monohydrate (75%) and microcrystalline cellulose (25%) (2.824 kg, 30.57% (w/w)), Crospovidone (784 g, 8.49% (w/w)) Talc (258 g, 2.79% (w/w)), Aerosil (26 g, 0.28% (w/w)), magnesium stearate (22 g, 0.24% (w/w)) and Sterotex (86 g, 0.093% (w/w)) were sieved and mixed together with the milled extrudate (5 kg, 54.13% (w/w)) using a planetary mixer until a homogenous mixture was obtained (15 minutes). All (w/w) percentages are based on the total weight of a film-coated tablet.

The mixture obtained was compressed on a Korsch tabletting machine operated at a speed of 10,800 tablets/hour and a compression pressure of 1500 to 1950 kg/cm² (147-191.1 Mpa). The length of the die was 19 mm, the breadth was 9.5 mm and the radius of the curvature 9.57 mm. The tablets had the following characteristics: nominal weight: 906.9 mg; maximum height: 5.88 mm; hardness: 11 daN; disintegration time: 2' 15"; friability: 0%.

The tablets were film-coated using a suspension comprising, by weight, HPMC 2910 5 mPa·s (8.5%), propylene glycol (2.1%), talc (1.7%), and and titanium dioxide (2.6%) in demineralised water (85%). HPMC 2910 5 mPa·s was added to the purified water and mixed until completely dispersed. The solution was left to stand until clear. Propylene glycol was added and mixed until uniform. Talc and titanium dioxide were added to the solution and mixed until uniform. The tablets were placed in a coating pan and the pigmented coating solution was sprayed onto the cores.

EXAMPLE 2

Multiple batches of itraconazole particles were prepared as set forth in example 1 (at a twin screw rate of 250 revolutions/min) with the following exceptions. The HPMC was acquired from Colorcon and was produced in Dow's Plaquemine plant ($d_{0.1}$=32 µm, $d_{0.5}$=92 µm, $d_{0.9}$=235 µm). The HPMC from this source had a markedly lower flowability. In view of the lower flowability, the throughput speed had to be lowered. This resulted in a prolonged transit time of the melt extrudate in the extruder and likely led to a higher energy input. The throughput was only 18±3 kg/h. The temperature of the extrusion dies was increased to get a smoother extrusion and avoid clogging. The temperature of the first, second and third compartment was 20° C., 190° C., and 190° C., respectively, the temperature of the transitional section was 205° C., the temperature at the die was 205° C.

Samples of ground extrudates of examples 1 and 2, respectively, were subjected to DSC analysis and the thermogram between −20° C. and 300° C. was obtained by heating the samples at a temperature rise rate of 10° C./minute. The endothem (J/g) at about 240° C. was determined.

The bioavailability of the tablets was determined according to the following protocol:

Methodology: Open, randomized, 2-way crossover, single oral-dose study, with a 14-day wash-out period in 56 healthy subjects after a standardized breakfast.

Number of subjects: 56 subjects (28 males, 28 females) included, administered and analyzed for safety, 52 included in bioequivalence evaluation. Diagnosis and main criteria for inclusion: Healthy male and female subjects, aged 18-55 years inclusive.

Test product, dose and mode of administration: 200-mg itraconazole melt-extrusion tablet. Single oral dose of one tablet with 240 mL of room temperature non-carbonated water after a standardized breakfast.

Reference product, dose and mode of administration: Sporanox® 100-img itraconazole capsules, Janssen Ortho LLC. Single oral dose of two capsules with 240 mL of room temperature non-carbonated water after a standardized breakfast.

Duration of treatment: Two study periods of 36 hours residency in the clinical center {−12 h until 24 h post-dose) with returns to the clinical center for the 36 h, 48 h, 72 h and 96 h blood samples post-dose, separated by a 14-day wash-out period, single dose administration during each period.

Statistical methods: Comparison of the pharmacokinetic parameters of itraconazole and hydroxy-itraconazole obtained after each treatment: ANOVA (model: formulations, subjects, gender, sequences and periods of administration) after log transformation.

The analysis of itraconazole and hydroxy itraconazole in human plasma was performed by HPLC-UV. The extraction method used was derived from the method described by Woestenborghs et al. (Journal of Chromatography, 413 (1987) 332-337). The components were detected by UV-absorption at 263 nm. Acquisition was performed using Millennium software of Waters. The 10-points calibration curves were fitted to the model $Y=A+B\cdot X$ using $1/X^2$ as weighing factor, where Y is the peak height ratio of itraconazole or hydroxy-itraconazole and the internal standard, X the nominal calibration level in ng/mL, A the intercept and B the slope. Unknowns were calculated using the formula: $X=(Y-A)/B$.

The results are summarized in the following table, where the $C_{max}$ and $AUC_t$ are given as point estimate in %, relative to the reference product:

| Example | Screw speed [rpm] | Endotherm at about 240° C. [J/g] | Bioavailability $C_{max}$ | $AUC_t$ |
|---|---|---|---|---|
| 1 | 200 | 0.49 (n = 6) | 69.4 | 76.9 |
| 1 | 250 | 0.29 (n = 6) | 82.4 | 84.3 |
| 2 | 250 | 0.10 (n = 2) | 102.2 | 116.7 |

As the above table indicates, a high energy input during melt extrusion production leads to improved bioavailability.

We claim:

1. A method for preparing a solid dispersion product comprising itraconazole and hydroxypropyl methylcellulose, which method comprises:
   a) blending itraconazole and hydroxypropyl methylcellulose;
   b) heating the blend to a temperature of 195 to 300° C. so as to obtain a homogenous melt and
   exerting a shearing and/or kneading action to the melt in an extruder selected from single screw extruders, intermeshing screw extruders and multi-screw extruders, wherein the screw(s) comprise(s) at least one of reverse-flighted elements, shear elements, kneading discs and rotor blades;
   c) forcing the thus obtained melt through one or more nozzles;
   d) allowing the melt to solidify to obtain a solid dispersion product; and
   e) optionally grinding the solid dispersion product;
wherein the temperature and the conditions of shearing and/or kneading in step b) are adjusted such that the solid dispersion product satisfies the formula $0.35 > \Delta H_{tr}$ wherein $\Delta H_{tr}$ represents the endotherm (J/g) accompanying a transition at an endothermic peak temperature in the range of from 240° C. to 250° C.

2. The method of claim 1, wherein forcing the melt is carried out at a temperature of 195 to 300° C.

3. The method of claim 2, additionally comprising compressing the ground solid dispersion product into a tablet.

4. The method of claim 1, additionally comprising sieving the ground solid dispersion product.

5. The method of claim 1, wherein the temperature and the conditions of shearing and/or kneading in step b) are adjusted such that the solid dispersion product satisfies the formula $0.20 > \Delta H_{tr}$ wherein $\Delta H_{tr}$ represents the endotherm (J/g) accompanying a transition at an endothermic peak temperature in the range of from 240° C. to 250° C.

6. The method of claim 1, wherein the solid dispersion product has a weight-average particle size ranging between 50 µm to 600 µm.

7. The method of claim 1, wherein the total content of methoxy and hydroxypropyl groups in the hydroxypropyl methylcellulose is in the range of 23 to 42% by weight.

8. The method of claim 7, wherein the methoxy group content is in the range of 19 to 30% by weight and the hydroxypropyl group content is in the range of 4 to 12% by weight.

9. The method of claim 8, wherein the hydroxypropyl methylcellulose has an apparent viscosity of from 3 to 15 mPa·s, as determined as a 2% by weight aqueous solution at 20° C.

10. The method of claim 1, wherein the weight ratio of itraconazole:hydroxypropyl methylcellulose is in the range of 1:1 to 1:17.

11. The method of claim 1, wherein the extruder used in step b) is a twin screw extruder.

* * * * *